US008147877B2

(12) United States Patent
DeAth et al.

(10) Patent No.: US 8,147,877 B2
(45) Date of Patent: *Apr. 3, 2012

(54) ESSENTIAL OILS BASED DISINFECTING COMPOSITIONS HAVING TUBERCULOCIDAL AND FUNGICIDAL EFFICACIES

(75) Inventors: S. Samuel DeAth, Ontario (CA); Larry Weiss, San Francisco, CA (US)

(73) Assignee: OhSo Clean, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/444,367

(22) Filed: Jun. 1, 2006

(65) Prior Publication Data

US 2007/0281039 A1 Dec. 6, 2007

(51) Int. Cl.
- A61K 36/00 (2006.01)
- A61K 36/53 (2006.01)
- A61K 36/73 (2006.01)

(52) U.S. Cl. ........ 424/725; 424/617; 424/745; 424/765; 424/736

(58) Field of Classification Search .......................... None
See application file for complete search history.

(56) References Cited

U.S. PATENT DOCUMENTS

| | | | |
|---|---|---|---|
| 3,697,641 A | 10/1972 | Ahrens | |
| 4,411,813 A | 10/1983 | Voisin | |
| 4,748,279 A | 5/1988 | Whiteley | |
| 4,952,398 A | 8/1990 | Tapin | |
| 5,094,842 A * | 3/1992 | Riley | 424/52 |
| 5,145,665 A * | 9/1992 | Klueppel et al. | 424/50 |
| 5,298,238 A * | 3/1994 | Hussein et al. | 424/49 |
| 5,403,587 A * | 4/1995 | McCue et al. | 424/736 |
| 5,437,858 A | 8/1995 | Hungerbach et al. | |
| 5,716,920 A | 2/1998 | Glenn, Jr. et al. | |
| 5,965,518 A | 10/1999 | Nakatsu et al. | |
| 6,010,933 A | 1/2000 | Cherng | |
| 6,010,993 A | 1/2000 | Romano et al. | |
| 6,022,459 A | 2/2000 | Briggs | |
| 6,048,836 A | 4/2000 | Romano et al. | |
| 6,106,838 A | 8/2000 | Nitsas | |
| 6,183,757 B1 | 2/2001 | Beerse et al. | |
| 6,183,763 B1 | 2/2001 | Beerse et al. | |
| 6,197,288 B1 * | 3/2001 | Mankoo | 424/76.1 |
| 6,210,695 B1 | 4/2001 | Beerse et al. | |
| 6,217,887 B1 | 4/2001 | Beerse et al. | |
| 6,255,268 B1 * | 7/2001 | Counts | 510/191 |
| 6,346,281 B1 * | 2/2002 | DeAth et al. | 424/725 |
| 6,585,961 B1 | 7/2003 | Stockel | |
| 6,613,728 B1 | 9/2003 | Sirianni et al. | |
| 6,649,660 B2 | 11/2003 | Ninkov | |
| 6,753,305 B2 | 6/2004 | Raso et al. | |
| 6,844,369 B2 | 1/2005 | Ninkov | |
| 6,846,498 B2 | 1/2005 | DeAth et al. | |
| 6,884,763 B2 | 4/2005 | Willard et al. | |
| 7,208,519 B2 | 4/2007 | Ninkov | |
| 2003/0091602 A1 * | 5/2003 | Witteler et al. | 424/401 |
| 2004/0057922 A1 * | 3/2004 | Schmid et al. | 424/70.13 |
| 2005/0137109 A1 * | 6/2005 | Quan et al. | 510/303 |
| 2005/0256018 A1 | 11/2005 | Keller et al. | |
| 2006/0024248 A1 * | 2/2006 | Spengler et al. | 424/49 |

FOREIGN PATENT DOCUMENTS

| | | |
|---|---|---|
| CH | 688 787 | 3/1998 |
| EP | 0842606 | 5/1998 |
| EP | 1 294 373 | 3/2003 |
| EP | 1278420 | 12/2005 |
| FR | 2599026 | 5/1986 |
| JP | 04321628 | 11/1992 |
| JP | 07076503 A * | 3/1995 |
| WO | WO 94/18939 | 9/1994 |
| WO | WO 96/11694 | 4/1996 |
| WO | WO 97/31093 | 8/1997 |

OTHER PUBLICATIONS

Hersch-Martinez et al, Antibacterial effects of commercial essential oils over locally prevalent pathogenic strains in Mexico, Fitoterapia 76 (2005) 453-457.*
Ansari et al, Evaluation of chemical constituents and trade potential of *Cymbopogon citratus* (lemongrass).*
Favel et al, Antifungal activity of steroidal glycosides from *Yucca gloriosa* L., Phytotherapy research, 19, 158-161, 2005.*
English Abstract of JP Application No. 04207359, Publication No. 06024952, Jan. 2, 1994, Patent Abstracts of Japan, European Patent Office.
Kurt Schnaubelt, Ph.D., Advanced Aromatherapy: The essential oil therapy, Healing Arts Press, Cologne, Germany, pp. 31-41, 1998.
Julia Lawless, The Illustrated Encyclopedia of Essential Oils; The complete guide to the use of oils in aromatherapy and herbalism, Element Books Limited, pp. 132, 139-141 and 228, 1996.
Matthew E. Levison, "Pharmacodynamics of antimicrobial drugs," Infect Dis Clin N Am 18 (2004) 451-465.

* cited by examiner

*Primary Examiner* — Qiuwen Mi
(74) *Attorney, Agent, or Firm* — Kilpatrick Townsend & Stockton LLP

(57) ABSTRACT

Disinfecting compositions having tuberculocidal and fungicidal efficacies for disinfecting and sanitizing inanimate surfaces is provided. The disinfecting compositions contain thyme oil or thyme oil and origanum oil, a salt of a transition metal, a biobased surfactant and water. This improved disinfecting composition is botanical, environmentally sustainable, non-toxic, mildly scented and highly stable.

20 Claims, No Drawings

ESSENTIAL OILS BASED DISINFECTING COMPOSITIONS HAVING TUBERCULOCIDAL AND FUNGICIDAL EFFICACIES

FIELD OF THE INVENTION

The present invention relates to disinfecting and sanitizing compositions, and more particularly to essential oils based compositions for disinfecting and sanitizing inanimate surfaces.

BACKGROUND OF THE INVENTION

There exist a wide variety of disinfecting compositions for eliminating microorganisms on inanimate surfaces. Many of these disinfecting compositions include toxic and poisonous chemicals that can cause serious effects on human health and our environment. When these disinfecting compositions are used on hard and inanimate surfaces such as counters and food preparation areas, bathroom fixtures, furniture and toys, precaution must be taken to ensure that the disinfecting compositions are rinsed off properly so that no residual toxic and poisonous chemicals remain on the surfaces. Further, with the use of synthetic chemicals, after extensive usage of these disinfecting compositions, the microorganisms have been shown to build up a tolerance or resistance to some of these synthetic chemicals, which reduces the efficacy of the disinfecting compositions. Moreover, synthetic chemicals can persist in the environment, which can be deleterious.

Some antimicrobial products containing naturally occurring essential oils are known to have antimicrobial properties. These products have been found to be effective in reducing or eliminating some microorganisms, typically those of vegetative bacteria and lipid or medium-sized viruses. However, since essential oils based antimicrobial products are not generally known to be effective against a wide spectrum of microorganisms, they are typically classified as sanitizers or perhaps as low-level or limited efficacy disinfectants by government regulatory bodies such as the United States Environmental Protection Agency (U.S. E.P.A.) or Health Canada. In order to achieve higher efficacy classifications such as hospital disinfectant, fungicide or tuberculocide, many of the available essential oils based antimicrobial products include synthetic co-actives such as quaternary ammonia, chlorine, phenol, alcohol, peroxides or acids. However, these synthetic co-actives are generally hazardous to the environment and have a negative impact on human health. As a result of the safety profiles of these synthetics, precautions need to be taken during handling and processing. In some instances, personal protective equipment is required when using these chemicals and stringent practices need to be followed when removing residues of these synthetics.

Still further, because essential oils are hydrophobic, they are not readily miscible in water. Often, a macroemulsion, a multiphasic or a viscous liquid is formed, which makes the essential oils difficult to process and poses problems when attempts are made to incorporate them into an aqueous solution. Due to the immiscibility of the essential oils into solution, aqueous antimicrobial compositions formulated with essential oils can be unstable, which results in an antimicrobial product with a short shelf life and poor aesthetic appeal. The immiscibility also contributes to the slow delivery of the essential oils to the microorganisms, thus leading to poor, slow or inconsistent killing results. In many instances, large concentrations of naturally occurring essential oils are required to achieve sufficient antimicrobial efficacy. Consequently, essential oils based antimicrobial products tend to be expensive.

U.S. Pat. Nos. 6,346,281 and 6,846,498 issued to the present inventor disclose aqueous antimicrobial compositions formulated with essential oils that are particularly effective at disinfecting and sanitizing inanimate surfaces. One of these compositions comprises about 0.5% to 10% by volume of a mixture of four essential oils, namely thyme oil, lemongrass, clove oil and eucalyptus oil, in a water carrier. Another of these compositions comprises about 0.5% to 10% by volume of at least one of the aforesaid essential oils and 1 to 1000 ppm of an ion agent such as copper sulfate that enhances the antimicrobial properties of the mixture of essential oils. Both of these compositions also require about 2 to 12% by volume of an organic solvent such as ethyl alcohol, hexadecane, n-propanol and ethyl acetate to disperse the essential oils into the water carrier. However, relatively large concentrations of each of the essential oils are required to provide these compositions with sufficient antimicrobial efficacy. Also, while both of these antimicrobial compositions are effective against a wide variety of gram negative and gram positive bacteria, they have not been demonstrated to be effective against some other types of microorganisms. Furthermore, the presence of clove oil in some of these compositions results in residue build-up on the inanimate surfaces and a strong, long-lasting fragrance that is not pleasing to some consumers.

Accordingly, there remains a need for improved disinfecting compositions that are environmentally sustainable, completely botanical or natural, biodegradable, non-toxic and capable of providing a broad disinfecting spectrum, and that utilize relatively low concentrations of a limited number of naturally occurring essential plant oils. There is also a need for improved essential oils based compositions that disperse the essential oils well in a water carrier, that do not require wiping or rinsing off after being applied to inanimate surfaces, and that are stable, have a long shelf life and are affordable and aesthetically appealing to consumers.

SUMMARY OF THE INVENTION

The present invention is directed to disinfecting compositions for disinfecting and sanitizing inanimate surfaces. The disinfecting compositions of the present invention comprise about 0.01% to about 0.6% by volume of thyme oil, about 0.001% to about 0.01% by volume of a salt of a transition metal, about 0.1% to about 10.00% by volume of at least one biobased surfactant and sufficient water to make up 100% by volume. These compositions are found to provide surprisingly high tuberculocidal and fungicidal efficacies.

In an embodiment of the present invention, the thyme oil in the disinfecting composition is present in an amount of about 0.1% to about 0.5% by volume.

In another embodiment of the present invention, the disinfecting composition further comprises about 0.01% to about 0.2% by volume of origanum oil, suitably about 0.05% to about 0.15% by volume.

According to the present invention, the transition metal is selected from copper, iron, zinc and silver. Suitably, the transition metal is copper.

Further, according to the present invention, the salt is selected from sulfate, chloride, gluconate, hydroxide, nitrate, oxide, carbonate and octanoate. More particularly, the salt is sulfate.

The biobased surfactant is selected from glucoside, sodium laurel ether sulphate, sodium laurel sulphate (SLS), sarcossinates, yucca, naturally derived sulfosuccinate, betaine, sultaine, propionate, acetate, amine oxide, naturally derived ammonium chloride, geminis, carboxylate, alcohol ethoxylate and combinations thereof. In an embodiment of the invention, the biobased surfactant is selected from glucoside, yucca, sodium laurel sulphate and combinations thereof. In a further embodiment of the invention, the glucoside is an alkylpolyglucoside.

Also within the scope of the present invention is a disinfecting composition which further comprises an essential oil based fragrance in an amount from about 0.01% to about 0.2% by volume, suitably from about 0.05% to about 0.15% by volume. The essential oil-based fragrance may be selected from rose oil, lavender oil and citrus oil. Particularly, the citrus oil may be orange, grapefruit, lime, lemon, lemongrass, blood orange, petitgrain and litsea cubeba. More particularly, the citrus oil is lemongrass.

The present invention therefore provides for improved disinfecting compositions which have a low level of essential oils and which are environmentally sustainable. The disinfecting compositions may be used as a tuberculocide, fungicide, virucide, bactericide, germicide or combinations thereof. Specifically, the disinfecting compositions of the present invention exhibit tuberculocidal and fungicidal efficacies. Moreover, the disinfecting compositions comprise substantially natural ingredients which are foods themselves or are listed as Food Additives or Generally Recognized As Safe by the F.D.A. Thus, no wiping or rinsing off of the disinfecting compositions of the present invention from the inanimate surfaces is required.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The improved disinfecting compositions of the present invention are environmentally sustainable, completely botanical or natural, biodegradable, non-toxic, mildly scented compositions having tuberculocidal and fungicidal efficacies for disinfecting and sanitizing inanimate surfaces. The disinfecting compositions utilize a naturally occurring essential oil, namely thyme oil, at a low concentration level. Thus, the disinfecting compositions of the present invention are mildly scented unlike the typical essential oils based antimicrobial products currently available. Further, the disinfecting compositions of the present invention utilize water as the sole solvent.

Specifically, the disinfecting composition of the present invention comprises:

(a) about 0.01% to about 0.6% by volume of thyme oil;
(b) about 0.001% to about 0.01% by volume of a salt of a transition metal;
(c) about 0.1% to about 10.00% by volume of at least one biobased surfactant; and
(d) sufficient water to make up 100% by volume.

As used herein, the expressions "environmentally sustainable", "natural", "green" "biobased" and "botanical" are understood to mean substances or mixtures that are derived from natural sources, whole or in part. Thus, these substances or mixtures have minimal environmental impact and require minimal non-renewable inputs when the entire life cycle of the chemical is studied. For example, "natural thyme oil" refers to thyme oil which is obtained from botanical sources whereas "synthetic thyme oil" refers to the oil of isolated thymol that is chemically synthesized from petroleum.

By "disinfecting", it is meant the destroying of over 99.99% of selected pathogenic and potentially pathogenic microorganisms, both gram negative and gram positive, on inanimate surfaces within 10 minutes under conditions prescribed by the appropriate government regulatory agency such as the U.S. E.P.A. or Health Canada. The government regulated term "high level disinfectant" as used herein refers to a disinfectant that kills all microbial pathogens, except large numbers of bacterial endospores, in no more than 10 minutes. This latter term also encompasses a disinfectant that kills tuberculosis. The government regulated term "low-level disinfectant" or "limited efficacy disinfectant" as used herein refers to a disinfectant that kills both or either of the selected gram negative and gram positive bacteria, respectively, but not pathogenic bacteria, in no more than 10 minutes.

The unregulated term "antibacterial" is used to mean capable of destroying an undefined number of microorganisms, but less then 99.9%, within an undefined period of time. The government regulated term "sanitizer" is used to mean capable of destroying 99.9% of bacteria in 5 minutes. Accordingly, the killing capability of a disinfectant is about 100 times greater than a sanitizer. The government regulated term "tuberculocidal" is used to mean capable of destroying over 99.99% of mycobacteria, particularly *Mycobacterium bovis* herein, in no more than 20 minutes. The government regulated term "fungicidal" is used to mean capable of destroying over 99.99% of selected fungi, particularly *Trichophyton mentagrophytes* herein, including their spores in no more than 10 minutes. The government regulated term "virucidal" is used to mean capable of destroying over 99.99% of selected viruses in no more than 10 minutes. The term "germicidal" is used to mean capable of destroying pathogenic and potentially pathogenic microorganisms. The term "bactericidal" is used to mean capable of destroying bacteria, but not necessarily bacterial spores or mycobacteria.

In accordance with the present invention, natural essential oils are used in the disinfecting compositions. Since these natural essential oils have not been refined or adulterated, they contain non-principal constituents which most likely contribute to the environmental and human health and safety profiles of the compositions, including their antimicrobial properties. As the mechanism of antimicrobial activity is most often unknown for natural essential oils, additional refining beyond the natural whole oil state is anticipated to modify the environmental and health and safety profiles in a negative fashion and possibly promote microbe evolutionary resistance. The thyme oil used in the present invention generally has over 50% thymol and thymol derivatives as well as about 3% to about 7% carvacrol and carvacrol derivatives while the origanum oil used in the present invention generally has about 60% carvacrol and carvacrol derivatives as well as about 3% to about 7% thymol and thymol derivatives so as to provide a base level of antimicrobial activities. Representative herbs from which thyme oil may be obtained include *Thymus vulgaris, Thymus serpyllium, Thymus capitatus, Thymus mastichina* and *Thymus zygus*. Representative herbs from which origanum oil may be obtained include *Origanum vulgar* or *Origanum dictamnus*. Of course, other herbs from which thyme oil and origanum oil or their principal constituents may be obtained are also possible as is readily recognized by persons skilled in the art.

Typically, the thyme oil present in the disinfecting composition is from about 0.01% to about 0.6% by volume. Suitably, the thyme oil present in the disinfecting composition is in an amount of about 0.1% to about 0.5% by volume.

In an embodiment of the present invention, the disinfecting composition further comprises about 0.01% to about 0.2% by volume of origanum oil, suitably about 0.05% to about 0.15% by volume of origanum oil.

The salt of a transition metal present in the disinfecting composition is typically about 0.001% to about 0.01% by volume. More suitably, the salt of the transition metal in the disinfecting composition is about 0.002% by volume. The transition metal may be selected from copper, iron, zinc and silver and the salt may be selected from sulfate, chloride, gluconate, hydroxide, nitrate, oxide, carbonate and octanoate. Suitably, in an embodiment of the disinfecting composition, the salt of the transition metal is copper sulfate.

The biobased surfactants of the present invention, when mixed with the natural essential oils, water and the salt of the transition metal, form a stable macroemulsion or microemulsion of the disinfectant composition. In other words, the biobased surfactant acts to help solubilize and disperse the natural essential oils, namely the thyme oil and the origanum oil, in the water. Typically, the disinfecting composition of the present invention comprises about 0.1% to about 10.00% by volume of at least one biobased surfactant. Suitably, the biobased surfactant is present in an amount of about 0.55% to about 8.00% by volume. More suitably, the biobased surfactant present in the disinfecting composition is about 0.75% by volume. The biobased surfactants contemplated by the present invention may be selected from glucoside, sodium laurel ether sulphate, sodium laurel sulphate, sarcossinates, yucca, naturally derived sulfosuccinate, betaine, sultaine, propionate, acetate, amine oxide, naturally derived ammonium chloride, geminis, carboxylate, alcohol ethoxylate and combinations thereof. Particularly, in an embodiment of the present invention, the biobased surfactant in the disinfecting composition is an alkylpolyglucoside. In another embodiment of the disinfecting composition of the present invention, the biobased surfactant is a combination of Glucopon™, a particular glucoside, yucca and sodium laurel sulphate. The advantage of using such biobased surfactants, for example, alkylpolyglucosides, over other types of surfactants is to maintain the benign environmental and human health and safety profiles of the disinfecting composition.

Water is included as a carrier in an amount sufficient to make the total composition 100% by volume. The pH of the disinfecting composition of the present invention ranges from about 0.2 to 8. Specifically, the pH of the disinfecting composition ranges from about 3.5 to 6.

One or more other ingredients may optionally be included in the disinfecting composition of the present invention to improve the aesthetic or other beneficial properties. Such optional ingredients may include fragrances, deodorizers, coloring agents, degreasing or descaling compounds, co-surfactants and the like. These additional optional ingredients, however, must be compatible with the other core components of the disinfecting composition and not negatively affect the environmental and the health and safety profiles of the composition of the present invention.

In an embodiment of the invention, the disinfecting composition further comprises an essential oil based fragrance. Particularly, the essential oil based fragrance is about 0.01% to about 0.2% by volume, suitably about 0.05% to about 0.15% by volume. Representative examples of an essential oil based fragrance are rose oil, lavender oil and citrus oil. The citrus essential oils may be selected from orange, grapefruit, lime, lemon, lemongrass, blood orange, petitgrain and litsea cubeba. In an embodiment of the invention, the citrus essential oil is lemongrass.

Since the components of the disinfecting compositions of the present invention originate from herbal essences, in admixture with inert substances, the disinfecting compositions of the present invention are readily degraded in the environment. Thus, they can be used sustainably, and without concern of environmental build up. As shown hereinafter in the experimental examples, the disinfecting compositions of the present invention also provide full and effective antimicrobial activities. It has been found that the particular combination of essential oils, namely thyme oil or thyme oil and origanum oil, with the salt of the transition metal and the biobased surfactant, once dissolved or dispersed in the water, each of which at particular concentration ranges, together exhibits unexpectedly good disinfectant properties against a broad spectrum of microorganisms with no adverse effects to human health or to the environment. The compositions are effective against microorganisms, and the microorganisms do not develop resistance to the compositions over time.

The disinfecting compositions of the present invention may be used as a tuberculocide, fungicide, virucide, bactericide, germicide or combinations thereof. Specifically, the disinfecting compositions of the present invention have demonstrated high tuberculocidal and fungicidal efficacies. More specifically, the disinfecting compositions of the present invention have been found to be effective against *Trichophyton mentagrophytes*, HIV Type I, *Mycobacterium bovis*, *Staphylococcus aureus*, *Pseudomonas aeruginosa* and *Salmonella choleraesuis*. The microbial reduction assays will be described hereinafter. The tuberculocidal efficacy of the disinfecting compositions was determined from the killing results of the microorganism *Mycobacterium bovis* whereas the fungicidal efficacy of the disinfecting compositions was determined from the killing results of the microorganism *Trichophyton mentagrophytes*. Due to the effectiveness of the disinfecting compositions of the present invention against tuberculocidal and fungicidal microorganisms, the disinfecting compositions are registered as an intermediate-level hospital-grade disinfectant, fungicide, tuberculocide and virucide in accordance to U.S. E.P.A. and Health Canada regulations.

Moreover, the disinfecting compositions of the present invention do not need to be wiped off or rinsed off since only natural, food-safe ingredients are included in the disinfecting compositions. This allows for longer contact with the inanimate surface area bearing the microorganisms, and as such ensures a higher killing rate and continuous germ control for extended period of time where desired. Further, since the disinfecting compositions of the present invention do not require wiping or rinsing to remove any disinfectant residues, the disinfecting compositions of the present invention are also convenient and easy to use. In addition, the disinfecting compositions of the present invention are non-corrosive, non-flammable, non-reactive, readily biodegradable, and have a very low volatile organic compound level of less than 1%.

Still further, it has been found that this particular combination of components provides a stable disinfecting composition which can withstand freezing. The disinfecting compositions of the present invention have been demonstrated to have a shelf life of at least 2 years.

The disinfecting compositions of the present invention may be formulated by conventional procedures known to one skilled in the art. For example, the disinfecting compositions can be formulated by combining the essential oils, salt of the transition metal, biobased surfactant and water together. The combined ingredients are then agitated or mixed until a macroemulsified or microemulsified solution of essential oils is formed.

The disinfecting compositions of the present invention may be formulated to be dispersed from a ready-to-use dispenser system. The disinfecting compositions can be dispelled from a trigger or finger pump bottle, a squeeze bottle or a pressurized sprayer to produce a spray, fog or foam. The disinfecting compositions of the present invention can also be incorporated into a towelette form or a gel carrier which can then be used to treat a variety of surfaces. The towelettes can be packaged individually or in bulk for individual distribution. Further, the disinfecting compositions of the present invention can be incorporated into other formulations or carriers having antimicrobial or disinfecting properties. These formulations may be those of hand sanitizers, antiseptics, soaps or lotions, dish or laundry soaps, deodorants, toothpastes, air fresheners. Still further, the disinfecting compositions of the present invention may be incorporated or impregnated into plastics to preserve the material and provide antimicrobial protection on its surfaces.

The disinfecting compositions contemplated by this invention can be used to disinfect inanimate or hard surfaces such as counters, food preparation surfaces and areas, eating utensils, bathroom fixtures such as sinks and toilets, tiles, floors, walls, windows, furniture, high chair trays, cribs, shopping cart handles, phones, toys, medical instruments and the like. They are also suitable for spraying into residential or commercials air ducts, heating, cooling and ventilation systems.

The following non-limiting examples are illustrative of the invention:

EXPERIMENTAL EXAMPLES

AOAC Germicidal Spray Products Test Principle:

A film of bacterial cells dried on a surface of glass slide carriers was exposed to a test substance for a specified contact time. After exposure, the carriers were transferred to vessels containing neutralized subculture media and assayed for survivors. Appropriate viability, carrier population and neutralization confirmation controls were performed. Sixty carriers were tested against each organism, each with 3 samples, and in which one of the samples was at least 60 days old. (180 carriers per sample; a total of 540 carriers). Plate count data, on appropriate culture media was performed on each test microorganism. It was determined that a concentration of at least $10^4$ microorganisms surviving the carrier-drying step is required. Exposure conditions including growth media, incubation, harvest and drying conditions, temperature, humidity and amount of spray released from the specified distance from the bacterial films were controlled and recorded. Killing on 59 out of each set of 60 carriers for an effective disinfectant product or 10 out of each set of 10 carriers for a fungicidal product, is used as a standard at a 95% confidence level. A kill is qualitatively determined by visual analysis of turbidity. If the carrier is clear, then total kill of the inoculum load has occurred. Partial kills or nearly total kills would be observed as turbid and therefore a fail.

Time Kill Test Assay for Antimicrobial Agents:

A suspension of bacterial cells was exposed to the test substance for specified contact times. After exposure, an aliquot of the suspension was transferred to a neutralizer and assayed for survivors. Appropriate purity, sterility, microorganism population and neutralization controls were performed. Kill results are expressed quantitatively in log reduction of the test organism within the specified contact time.

The above described methodologies are two examples which may be adapted for testing the efficacies of the disinfectant product as required by governing agencies.

Example 1

Disinfecting compositions were prepared, having ingredients of the amount in v/v % specified in Table 1 as follows:

TABLE 1

| Components | Disinfecting Compositions | | | | | | |
|---|---|---|---|---|---|---|---|
| | F38 | D56 | D64 | D66 | F68 | F76 | F102 |
| Thyme Oil | 0.5 | 0.250 | 0.125 | 0.125 | 0.5 | 0.5 | 0.5 |
| Lemongrass oil | 0.1 | | | 0.05 | 0.1 | 0.1 | 0.1 |
| Clove Oil | 0.1 | | | | | | |
| Origanum oil | | | 0.125 | 0.125 | | | 0.1 |
| Alkylpolyglucoside | 0.75 | | | | | 0.75 | 0.75 |
| Glucopon | | 5.0 | 5.0 | 5.0 | | | |
| SLS | | 2.6 | 2.6 | 2.6 | | | |
| Ethanol | | | | | | 1.5 | |
| Yucca | | | | | | 0.2 | |
| Copper Sulfate | 0.001 | 0.002 | 0.002 | 0.002 | 0.002 | 0.001 | 0.002 |
| Water | to 100% | to 100% | to 100% | to 100% | to 100% | to 100% | to 100% |

Example 2

The efficacy of disinfecting compositions F38, D56, D64, D66, F68, F76 and F102 against the microorganism *Staphylococcus aureus* was determined. The data in Table 2 shows that all of the compositions with the listed essential oils exhibited antimicrobial activity. However, to be considered as a highly effective disinfecting composition, an antimicrobial reduction greater than 4 log is generally required. Accordingly, the disinfecting compositions F38, F68 and F102 are the most effective compositions from the group of disinfecting compositions tested.

TABLE 2

| Organisms: *Staphylococcus aureus* | Disinfecting Compositions | | | | | | |
|---|---|---|---|---|---|---|---|
| | F38 | D56 | D64 | D66 | F68 | F76 | F102 |
| Time Kill | >6 log @ 5 min. | 1.1 log @ 10 min. | 2.1 log @ 10 min. | 2.1 log @ 10 min. | >6 log @ 1 min. | 4.9 log @ 10 min. | >6 log @ 1 min. |

The data shows that disinfecting compositions F38, F68 and F102 which have a greater amount of thyme oil content and an alkylpolyglucoside as the biobased surfactant are more effective against *Staphylococcus aureus* than disinfecting compositions D56, D64 and D66 which have a lower thyme oil content and include the combination of Glucopon and sodium laurel sulphate as the biobased surfactants. The data also shows that disinfecting compositions F38, F68 and F102 which have an alkylpolyglucoside as the biobased surfactant are more effective against *Staphylococcus aureus* than disinfecting composition F76 which has yucca as the biobased surfactant. Further, the inclusion of the solvent, ethanol, in disinfecting composition F76 does not improve the antimicrobial efficacy of the composition. Although both disinfecting compositions F38 and F102 demonstrate high antimicrobial efficacy against *Staphylococcus aureus*, it is apparent from the data that the inclusion of origanum oil enhances the antimicrobial efficacy of disinfecting composition F102.

Example 3

As shown in Table 3 below, the disinfecting compositions F68 and F102 were successfully tested against *Trichophyton mentagrophytes*. The killing results of the microorganism *Trichophyton mentagrophytes* were used to determine the fungicidal efficacy of the disinfecting compositions. The disinfecting compositions showing antimicrobial reduction greater than or equal to 5 log are generally considered to be highly effective.

TABLE 3

| Organisms: | Disinfecting Compositions | |
| --- | --- | --- |
| *Trichophyton mentagrophytes* | F68 | F102 |
| Time Kill | >6 log @ 3 min. | >6 log @ 1 min. |

Example 4

As shown in Table 4 below, the disinfecting composition F102 was successfully tested against *Mycobacterium bovis* and HIV Type I. The killing results of the microorganism *Mycobacterium bovis* were used to determine the tuberculocidal efficacy of the disinfecting composition. The data shows that disinfecting composition F102 is effective against both *Mycobacterium bovis* and HIV Type I.

TABLE 4

| Disinfecting Composition | Organisms | Time Kill |
| --- | --- | --- |
| F102 | *Mycobacterium bovis* | >6 log @ 5 min. |
| F102 | HIV Type I | >4 log @ 10 min. |

Example 5

As shown in Table 5 below, the disinfecting composition was successfully tested against *Salmonella choleraesuis* and *Pseudomonas aeruginosa*.

TABLE 5

| Disinfecting Composition | Organisms | Time Kill |
| --- | --- | --- |
| F38 | *Salmonella choleraesuis* | >5 log @ 10 min. |
| F38 | *Pseudomonas aeruginosa* | >4 log @ 10 min. |

Example 6

A primary skin irritation study in rabbits was performed. The test results indicate that the disinfecting composition of the present invention has a Primary Dermal Irritation Index (PDI) of 0.3 which is within the safety rating category allowed by the U.S. E. P.A. for scoring primary skin irritation risk.

Example 7

A primary eye irritation study in rabbits was performed. The test results indicate that the disinfecting composition of the present invention has a primary eye irritation maximum mean total score of 7.7 which is also within the safety rating category allowed by the U.S. E.P.A. for scoring ocular lesions and eye irritation.

Example 8

Residential Exposure Assessments of the disinfecting composition of the present invention in HVAC Systems were performed. The results indicate that the disinfecting composition of the present invention has 1-hour and 4-hour maximum exposures to thyme oil in residential HVAC systems which are respectively 102,000- and 47,000-fold less than the acute oral $LD_{50}$ in rats of 4,700 mg/kg for thyme oil. Thus, the anticipated short-term exposures with the use of the present invention in residential HVAC systems are more than 4 to 5 orders of magnitude below available acute toxicological benchmarks, according to The Multi-Chamber Concentration and Exposure Model, developed for the Environmental Monitoring Systems Laboratory, U.S. E.P.A., Las Vegas, Nev. (U.S. E.P.A. 1991a), which is within the safety rating category allowed by the U.S. E.P.A.

We claim:

1. A disinfecting composition for disinfecting and sanitizing inanimate surfaces consisting essentially of:
- (a) about 0.01% to about 0.6% by volume of thyme oil;
- (b) about 0.001% to about 0.01% by volume of a salt of copper;
- (c) about 0.5% to about 10% by volume of at least one biobased surfactant; and
- (d) sufficient water to make up 100% by volume.

2. The disinfecting composition according to claim 1, wherein the thyme oil is present in an amount in the range of about 0.1% to about 0.5% by volume.

3. The disinfecting composition according to claim 1, wherein the salt is selected from the group consisting of sulfate, chloride, gluconate, hydroxide, nitrate, oxide, carbonate and octanoate salts.

4. The disinfecting composition according to claim 1, wherein the salt copper is copper sulfate.

5. The disinfecting composition according to claim 1, wherein the biobased surfactant is present in an amount in the range of about 0.55% to about 8% by volume.

6. The disinfecting composition according to claim 1, wherein the biobased surfactant is selected from the group consisting of sodium lauryl ether sulphate, sodium lauryl sulphate, sarcossinates, sulfosuccinate, betaine, sultaine, propionate, acetate, amine oxide, ammonium chloride, geminis, carboxylate, alcohol ethoxylate, and combinations thereof.

7. The disinfecting composition according to claim 1, wherein the biobased surfactant is selected from the group consisting of glucoside, sodium lauryl sulphate, and combinations thereof.

8. The disinfecting composition according to claim 1, wherein the at least one biobased surfactant is alkylpolyglucoside.

9. The disinfecting composition according to claim 1, wherein the composition causes at least a 4 log reduction in microbes in 60 seconds.

10. A disinfecting composition for disinfecting and sanitizing inanimate surfaces consisting essentially of:
 (a) about 0.01% to about 0.6% by volume of thyme oil;
 (b) about 0.001% to about 0.01% by volume of a salt of copper;
 (c) about 0.01% to about 0.2% by volume of origanum oil;
 (d) about 0.1% to about 10% by volume of at least one biobased surfactant; and
 (e) sufficient water to make up 100% by volume.

11. The disinfecting composition according to claim 10, wherein the salt is selected from the group consisting of sulfate, chloride, gluconate, hydroxide, nitrate, oxide, carbonate and octanoate salts.

12. The disinfecting composition according to claim 10, wherein the biobased surfactant is selected from the group consisting of sodium lauryl ether sulphate, sodium lauryl sulphate, sarcossinates, sulfosuccinate, betaine, sultaine, propionate, acetate, amine oxide, ammonium chloride, geminis, carboxylate, alcohol ethoxylate, and combinations thereof.

13. The disinfecting composition according to claim 10, wherein the at least one biobased surfactant is alkylpolyglucoside.

14. The disinfecting composition according to claim 10, wherein the composition causes at least a 4 log reduction of microbes in 60 seconds.

15. A disinfecting composition for disinfecting and sanitizing inanimate surfaces consisting essentially of:
 (a) about 0.01% to about 0.6% by volume of thyme oil;
 (b) about 0.001% to about 0.01% by volume of a salt of copper;
 (c) about 0.5% to about 10% by volume of at least one biobased surfactant;
 (d) an essential oil based fragrance; and
 (e) sufficient water to make up 100% by volume.

16. The disinfecting composition according to claim 15, wherein the essential oil based fragrance has a concentration in the range of about 0.01% to about 0.2% by volume.

17. The disinfecting composition according to claim 16, wherein the essential oil-based fragrance is present in a concentration in the range of about 0.05% to about 0.15% by volume.

18. The disinfecting composition according to claim 15, wherein the essential oil-based fragrance is selected from the group consisting of rose oil, lavender oil and citrus oils.

19. The disinfecting composition according to claim 18, wherein the citrus oil is obtained from lemongrass.

20. A disinfecting composition for disinfecting and sanitizing inanimate surfaces comprising:
 (a) about 0.01% to about 0.6% by volume of thyme oil;
 (b) about 0.001% to about 0.01% by volume of a salt of copper;
 (c) about 0.5% to about 10% by volume of at least one biobased surfactant; and
 (d) sufficient water to make up 100% by volume
wherein the composition (i) contains less than 1% of volatile organic solvents and (ii) is in the form of an emulsion.

* * * * *